US00PP28608P3

(12) United States Plant Patent
Suphachadiwong

(10) Patent No.: US PP28,608 P3
(45) Date of Patent: Nov. 7, 2017

(54) *VANDA* PLANT NAMED 'SPCDW1515'

(50) Latin Name: ***Vanda* Jones ex R. Br.**
Varietal Denomination: SPCDW1515

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/330,348

(22) Filed: Sep. 9, 2016

(65) Prior Publication Data

US 2017/0142887 P1 May 18, 2017

(30) Foreign Application Priority Data

Sep. 15, 2015 (QZ) ..... PBR 2015/2164

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Samuel R. McCoy, Jr.

(57) ABSTRACT

A new and distinct *Vanda* cultivar named 'SPCDW1515' which is characterized by sepals and petals which are white to purple-violet and blotched violet, sepals and petals which are heavily dotted and marbled violet to violet-blue, a labellum with lateral lobes which are white and fading to yellow and a violet to violet-blue central lobe, as well as the stability of these characteristics from generation to generation.

4 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1515'.

CROSS REFERENCE TO RELATED APPLICATIONS

This application claims priority to the Community Plant Variety Rights application number 2015/2164, filed Sep. 15, 2015, which is herein incorporated by reference.

BACKGROUND OF THE INVENTION

Parentage: The *Vanda* variety 'SPCDW1515' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in September of 2004.

The new variety was first selected in December of 2009, in a research greenhouse in Bangphra, Thailand belonging to the inventor. After identifying the new variety as a potentially interesting selection, the inventor continued confidential testing and propagation of 'SPCDW1515', assessing stability of the unique characteristics of this variety.

Asexual Reproduction: Asexual reproduction of the new cultivar 'SPCDW1515', by way of mericloning, was first initiated in October of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1515' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1515'. These characteristics in combination distinguish 'SPCDW1515' as a new and distinct *Vanda* cultivar:

1. *Vanda* 'SPCDW1515' exhibits sepals and petals which are white to purple-violet and blotched violet; and
2. *Vanda* 'SPCDW1515' exhibits sepals and petals which are heavily dotted and marbled violet to violet-blue; and
3. *Vanda* 'SPCDW1515' exhibits a labellum with lateral lobes which are white and fading to yellow, and a violet to violet-blue central lobe.

BOTANICAL DESCRIPTION OF THE PLANT

Figure 1:
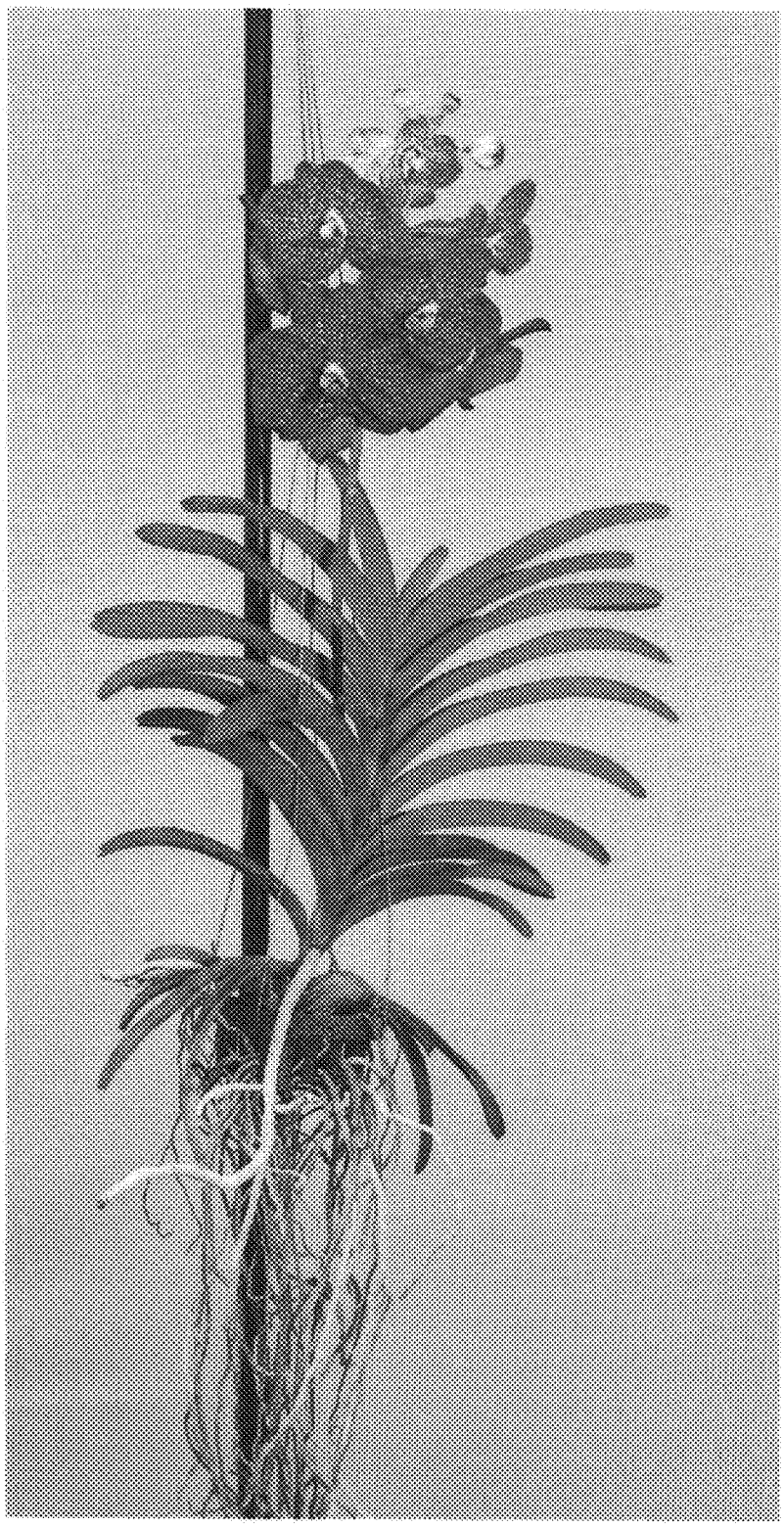
FIG. 1 illustrates, as nearly true as it is reasonably possible to make the same in color photographs of this type, an exemplary plant of 'SPCDW1515' grown in a commercial greenhouse in Honselersdijk, the Netherlands. This plant is approximately 6 years old from the time of mericloning, shown planted in an 8 by 8 cm container.
Figure 2:
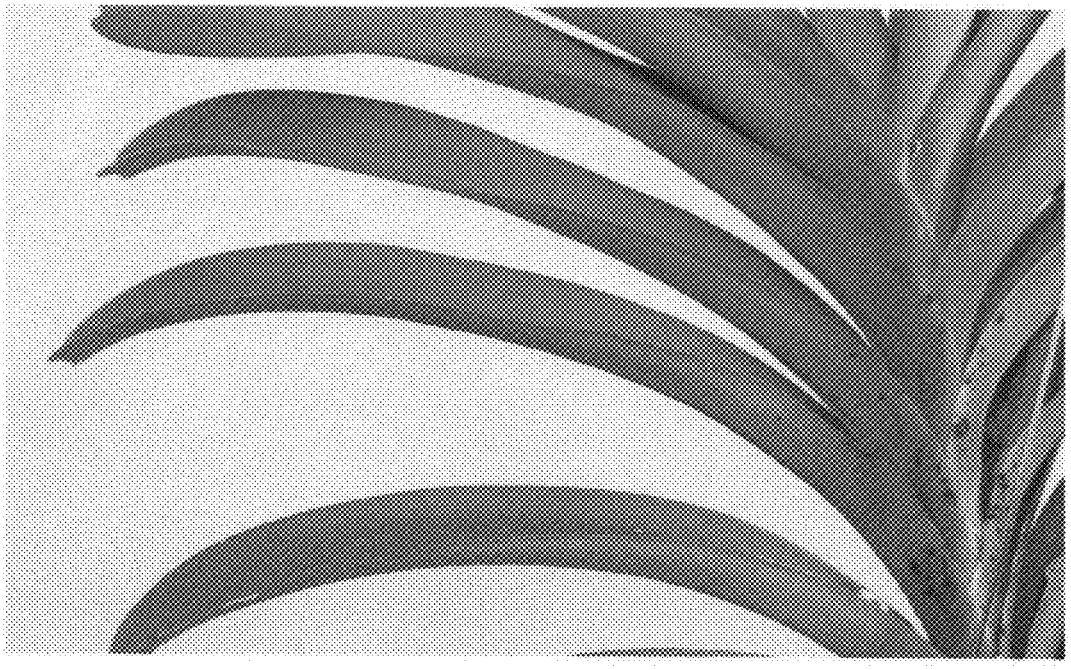
FIG. 2 illustrates, as nearly true as it is reasonably possible to make the same in color photographs of this type, the typical foliage of 'SPCDW1515'.
Figure 3:
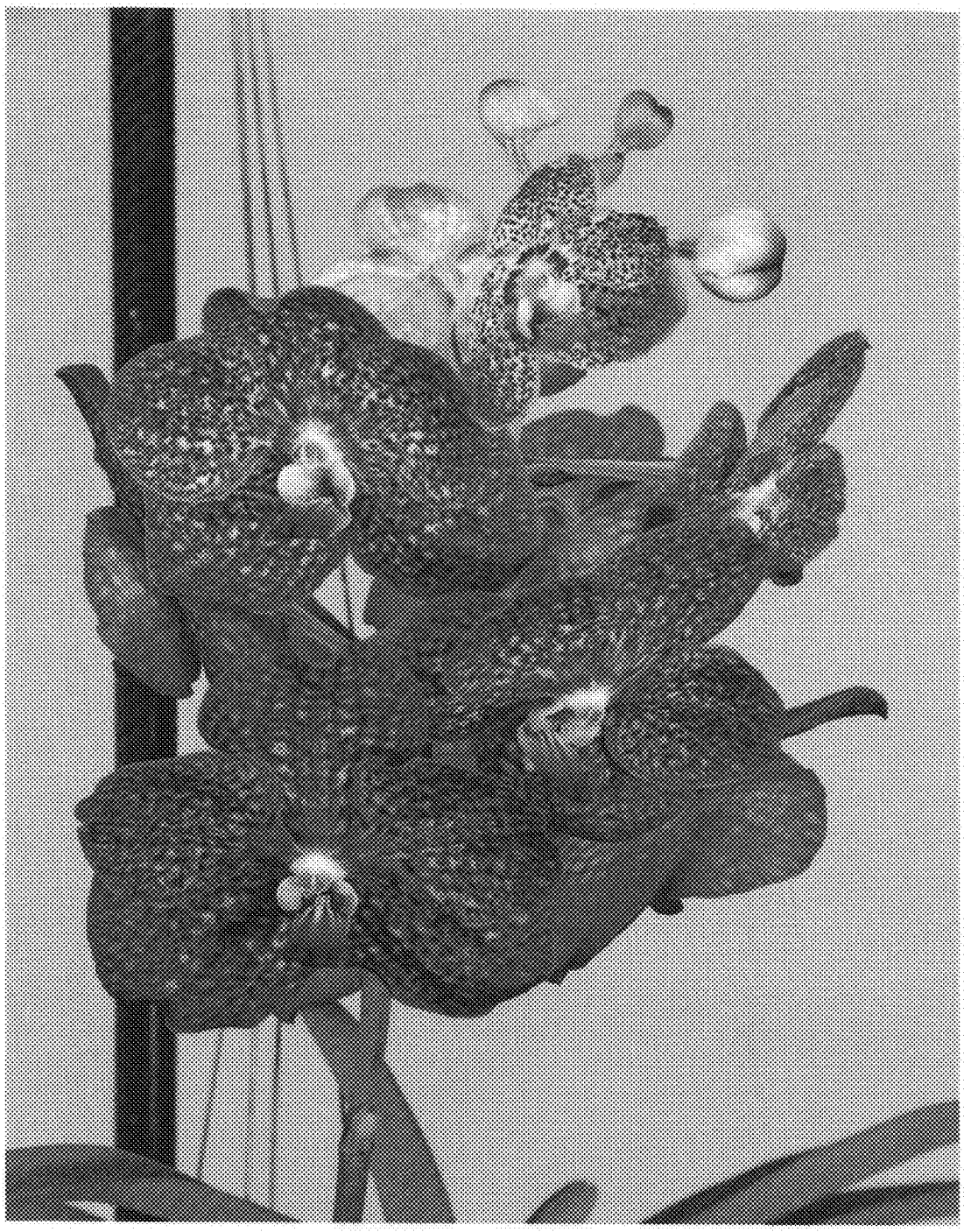
FIG. 3 illustrates, as nearly true as it is reasonably possible to make the same in color photographs of this type, the typical inflorescence of 'SPCDW1515'.
Figure 4:
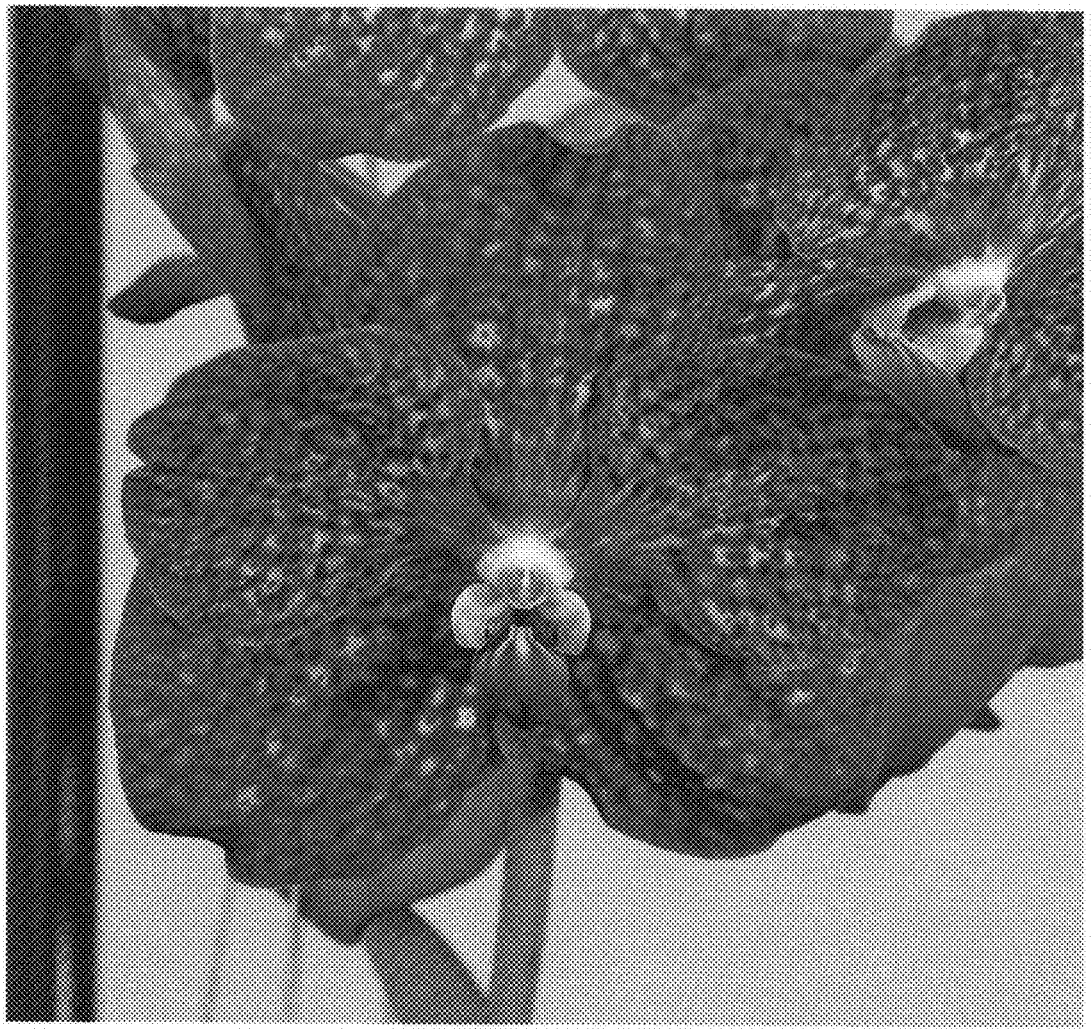
FIG. 4 illustrates, as nearly true as it is reasonably possible to make the same in color photographs of this type, the typical flower of 'SPCDW1515'.

The following observations and measurements made in August of 2016 describe averages from a sample set of six specimens of six year-old 'SPCDW1515' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1515' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1515' and comparisons with other varieties of *Vanda* are provided below.

Plant description:

- *Growth habit.*—Perennial; monopodial, upright. Single monopodial leafy stem, with flowers carried slightly above the leaf plane with inflorescences growing from the leaf axils.
- *Average height from base (plant grown in hanging basket, so no soil line present) to foliar plane.*—36.0 cm.
- *Average height from base (plant grown in hanging basket, so no soil line present) to top of floral plane.*—55.5 cm.
- *Plant spread.*—Average of 35.7 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—56.9 cm long with a diameter of 0.4 cm, on average.
- *Texture.*—Very fleshy; non-fibrous.
- *Color.*—Greyed-Green, near RHS 192A to 192B; root apex is yellow-green, RHS 147A to 147B.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—24.0 cm.
- *Diameter.*—1.1 cm.
- *Internode length.*—1.0 cm.
- *Luster.*—Matte.
- *Aspect.*—Near vertical.
- *Strength.*—Very strong.
- *Color, juvenile.*—Yellow-green, in between near RHS 150C and 150D.
- *Color, mature.*—Yellow-green, in between near RHS 150C and 150D.
- *Color at internodes.*—Yellow-green, in between near RHS 150C and 150D.
- *Pubescence.*—Glabrous.

Foliage:

- *Arrangement.*—Distichous.
- *Dimensions.*—18.4 cm long and 2.3 cm wide, on average.
- *Shape of blade.*—Ligulate; strongly carinate.
- *Aspect.*—Moderately curved.
- *Apex.*—Unequal praemorse.
- *Base.*—Sheathing.
- *Sheath dimensions.*—3.0 cm long and 1.2 cm wide, on average.
- *Sheath color.*—Yellow-green, near RHS 145B and 145C.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Juvenile foliage, adaxial surface — Green, near RHS 143B to 143C, and darker towards the margins, near NN 137B. Juvenile foliage, abaxial surface — Green, near RHS 143B to 143C. Mature foliage, adaxial surface — Green, near RHS 143A. Mature foliage, abaxial surface — In between green, RHS 143C, and yellow-green, RHS 144A.
- *Venation.*—Parallel.
- *Venation color, adaxial surface.*—Green, near RHS 143A.
- *Venation color, abaxial surface.*—In between green, RHS 143C, and yellow-green, RHS 144A.
- *Petiole.*—No petioles present; leaves sessile.

Inflorescence:

- *Inflorescence arrangement.*—Axially placed raceme.
- *Natural flowering season.*—Autumn into winter.

*Time to flower.*—Approximately 10 months.

*Flowers per inflorescence.*—Average of 13; 10 open flowers and 3 buds.

*Inflorescence height.*—Approximately 21.6 cm (measured from base of lowest flower to top of upper flower).

*Inflorescence diameter.*—Approximately 17.6 cm.

*Peduncle.*—Dimensions — Approximately 40.2 cm long and 0.7 cm wide. Aspect — Generally at a 30 degree angle to lateral branch axis, varying between 20 and 40 degrees. Strength — Moderately strong. Texture and luster — Glabrous and moderately glossy. Color — Green, near RHS 143B to 143C.

Bud:

*Length.*—Average of 1.7 cm.

*Diameter.*—Average horizontal diameter is 1.6 cm; the vertical diameter is 2.0 cm.

*Shape.*—Cubic, with a deltoid apex which is pointed downward.

*Pubescence, texture and luster.*—Glabrous, smooth and matte.

*Color.*—Yellow-green, near RHS 145D; apex is purple, near RHS 79D.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 10.2 cm.

*Diameter.*—Approximately 9.8 cm.

*Depth.*—Approximately 3.5 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 4.6 cm. Width — Approximately 4.5 cm. Shape — Near orbicular. Apex — Obtuse. Base — Cuneate. Margin — Entire; slightly undulated. Pubescence, texture and luster of upper surface — Glabrous, velvety and matte. Pubescence, texture and luster of lower surface — Glabrous, velvety and matte. Color when opening, upper surface — White, near RHS NN155D, and blotched violet, near RHS N87C to N87D; moderately to heavily dotted violet to violet-blue, in between RHS 83A and N92A. Color when opening, lower surface — White, near RHS NN155A, and tinged violet-blue particularly towards the apex and margins, near RHS 90D and lighter. Color when fully opened, upper surface — Purple-violet, near RHS N82C and N82D, and blotched violet, near RHS 86B and N87A; heavily dotted violet to violet-blue, in between RHS 83A and N92A. Color when fully opened, lower surface — Violet, near RHS 85C and 85D, and fading darker towards the top, near RHS N88C. Fading, upper surface — Not fading. Fading, lower surface — Not fading. Venation — Densely reticulate. Venation color, fully opened, upper surface — Purple-violet, near RHS N82C and N82D, and blotched violet, near RHS 86B and N87A. Venation color, fully opened, lower surface — Violet, near RHS N88B.

*Labellum.*—Shape — Three-lobed, lateral lobes are involute and the central lobe is revolute. Length — Central lobe — Approximately 2.0 cm. Lateral lobes — Approximately 0.7 cm. Width — Central lobe — Approximately 1.1 cm. Lateral lobes — Approximately 0.7 cm. Apex, central lobe — Emarginate. Apex, lateral lobes — Obtuse. Base, central and lateral lobes — Cuneate. Margin, central lobe — Entire; revolute and slightly undulated. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Violet, near RHS 86C to 86D. Lateral lobes — White, near RHS 155A, and fading to yellow, RHS 11B, towards the base. Color when opening, lower surface — Central lobe — Violet, near RHS 86D, and fading to white, near RHS 155C, towards the base. Lateral lobes — White, near RHS 155B. Color when fully opened, upper surface — Central lobe — Violet, near RHS 86A, and fading to violet-blue at the apex, RHS N89B. Lateral lobes — White, near RHS 155A, and fading to yellow, RHS 6C, towards the base; tinged purple-violet towards the apex, RHS N82D. Color when fully opened, lower surface — Central lobe — Violet-blue, near RHS N92B, and fading lighter towards the base, near RHS 91C. Lateral lobes — White, near RHS 155B, and tinged violet at the apex, RHS 86D. Fading, upper surface — Not fading. Fading, lower surface — Not fading. Venation — Densely reticulate. Venation color, fully opened, upper surface — Central lobe — Violet, near RHS 86A, and fading to violet-blue at the apex, RHS N89B. Lateral lobes — White, near RHS 155A, and fading to yellow, RHS 6C, towards the base; tinged purple-violet towards the apex, RHS N82D. Venation color, fully opened, lower surface — Central lobe — Violet-blue, near RHS N92B, and fading lighter towards the base, near RHS 91C. Lateral lobes — White, near RHS 155B, and tinged violet at the apex, RHS 86D.

*Callosities.*—Dimensions — 1.5 cm long and 0.8 cm wide, on average. Color — White, near RHS N155A.

*Spurs.*—Quantity — Average of 1. Length — Approximately 0.6 cm. Diameter — Approximately 0.4 cm. Vertical height — Approximately 0.5 cm, at the base. Shape — Short triangular. Apex — Bluntly acute. Base — Broad Cuneate. Pubescence, texture and luster — Glabrous, smooth, and matte. Color — Violet, near RHS 85D, and very slightly striped darker, near RHS 85B to 85C.

*Sepals.*—Quantity — Average of 3 unfused sepals. Arrangement — One dorsal sepal and two lateral sepals. Length — Dorsal sepal — Approximately 4.9 cm. Lateral sepals — Approximately 5.0 cm. Width — Dorsal sepal — Approximately 4.7 cm. Lateral sepals — Approximately 5.6 cm. Shape — Dorsal sepal — Broad ovate. Lateral sepals — Near orbicular. Apex, dorsal and lateral sepals — Obtuse.

Base, dorsal and lateral sepals — Cuneate. Margin, dorsal and lateral sepals — Entire; dorsal sepal are non-undulated and lateral sepals are slightly undulated. Pubescence, texture and luster — Glabrous, velvety, and matte on both the upper and lower sepal surfaces. Color when opening, upper surface — Dorsal sepal — White, near RHS NN155D, and blotched violet, near RHS N87C and N87D; sepals are moderately to heavily dotted violet to violet-blue, in between RHS 83A and N92A. Lateral sepals — White, near RHS NN155D, and blotched violet, near RHS 86C and 86D; sepals are moderately to heavily dotted violet to violet-blue, in between RHS 83A and N92A. Color when opening, lower surface — Dorsal sepal — Violet, near RHS 85C to 85D, and fading darker towards the apex, near RHS 86B to 86C. Lateral sepals — Violet, near RHS 85C to 85D, and fading darker towards the apex, near RHS 86B to 86C. Color when fully opened, upper surface — Dorsal sepal — White, near RHS NN155A, and blotched violet, RHS N88B; sepals are heavily dotted and marbled darker, near RHS 86A. Lateral sepals — White, near RHS NN155A, and blotched violet, RHS N88B; sepals are heavily dotted and marbled darker, near RHS 86A. Color when fully opened, lower surface — Dorsal sepal — Violet, near 85C and 85D, and fading darker towards the apex, near RHS N88C. Lateral sepals — Violet, near 85C and 85D, and fading darker towards the apex, near RHS N88C. Fading, upper surface — Not fading. Fading, lower surface — Not fading. Venation — Densely reticulate. Venation color, fully opened, upper surface — Dorsal sepal — White, near RHS NN155A, and blotched violet, RHS N88B; sepals are heavily dotted and marbled darker, near RHS 86A. Lateral sepals — White, near RHS NN155A, and blotched violet, RHS N88B; sepals are heavily dotted and marbled darker, near RHS 86A. Venation color, fully opened, lower surface — Dorsal sepal — Violet-blue, near RHS 90D, and fading violet towards the apex, in between near N88B and N88C. Lateral sepals — Violet-blue, near RHS 90D, and fading violet towards the apex, in between near N88B and N88C.

*Pedicels.*—Length — Approximately 5.4 cm. Diameter — Approximately 0.5 cm. Angle — Approximately 75 degree angle to peduncle axis. Strength — Moderate. Texture — Glabrous, axially angled with 5 "ribs", axially twisted (due to resupination). Luster — Glossy. Color — Purple-violet, near RHS N82B.

*Bract.*—Quantity — One bract present at the base of each pedicel. Shape — Broad ovate; folded around the base of each pedicel. Dimensions — Average of 1.3 cm long and 1.3 cm wide. Apex — Broad acute. Base — Broad cuneate. Margins — Entire. Color, both surfaces — Yellow-green, near RHS N144B.

Reproductive organs:

*Column.*—Length — Approximately 0.5 cm. Diameter — Approximately 0.6 cm. Color — White, NN155A, and tinged purple-violet, N82B.

*Ovary.*—Position — Inferior. Diameter — Approximately 0.3 cm. Color — Yellow-green, RHS 150C.

*Pollinia color.*—Yellow-orange, RHS 14A.

Seed and fruit: No fruit and seed production has been detected to date.

COMPARISON WITH THE PARENT PLANTS

Plants of the new cultivar 'SPCDW1515' differ from the unnamed *Vanda* seed parent (not patented) by the characteristics described in Chart 1.

CHART 1

| Characteristic | 'SPCDW1515' | Unnamed seed parent |
|---|---|---|
| Flower color. | Background color is a darker violet-blue. | Background color is a lighter blue. |
| Flower color pattern. | Heavily dotted. | Lightly dotted. |
| Inflorescence. | More flowers on each raceme compared to the seed parent. | Fewer flowers on each raceme compared to the 'SPCDW1515'. |
| Flower size. | Smaller than the seed parent. | Larger than 'SPCDW1515'. |
| Plant size. | More compact than the seed parent. | Larger than 'SPCDW1515'. |
| Plant vigor. | More vigorous; easier to cultivate and quicker to flower when compared to the seed parent. | Less vigorous; more difficult to cultivate and slower to flower when compared to 'SPCDW1515'. |

Plants of the new cultivar 'SPCDW1515' differ from the unnamed *Vanda* pollen parent (not patented) by the characteristics described in Chart 2.

CHART 2

| Characteristic | 'SPCDW1515' | Unnamed pollen parent |
|---|---|---|
| Flower color. | Non-uniform violet-blue. | Uniform dark violet-blue. |
| Inflorescence. | Fewer flowers on each raceme compared to the seed parent. | More flowers on each raceme compared to the 'SPCDW1515'. |
| Flower size. | Larger than the pollen parent. | Smaller than 'SPCDW1515'. |
| Plant size. | Larger than the pollen parent. | Smaller than 'SPCDW1515'. |

COMPARISON WITH THE MOST SIMILAR *VANDA* CULTIVAR KNOWN TO THE INVENTOR

Plants of the new cultivar 'SPCDW1515' are most similar to the cultivar, *Vanda* 'Princess Mikasa' (not patented in the United States). A comparison of 'SPCDW1515' with *Vanda* 'Princess Mikasa' is described in Chart 3.

CHART 3

| Characteristic | 'SPCDW1515' | 'Princess Mikasa' |
|---|---|---|
| Leaf length. | 18.4 cm. | 22.2 cm. |
| Flower, vertical height. | 10.2 cm. | 9.3 cm. |
| Flower, diameter. | 9.8 cm. | 9.2 cm. |
| Petal color; upper surface, when opening. | White, near RHS NN155D, and blotched violet, near RHS N87C to N87D; moderately to heavily dotted violet to violet-blue, in between RHS 83A and N92A. | Violet, near RHS N88C, and veined darker, RHS 86B to 86C; lower part of petal finely dotted violet, near RHS 86A to 86B. |

CHART 3-continued

| Characteristic | 'SPCDW1515' | 'Princess Mikasa' |
|---|---|---|
| Petal color; lower surface, when opening. | White, near RHS NN155A, and tinged violet-blue particularly towards the apex and margins, near RHS 90D and lighter. | Violet, near RHS N88C, and veined darker, RHS 86B to 86C. |
| Petal color; upper surface, when fully open. | Purple-violet, near RHS N82C and N82D, and blotched violet, near RHS 86B and N87A; heavily dotted violet to violet-blue, in between RHS 83A and N92A. | Violet, near RHS N87C. |
| Petal color; lower surface, when fully open. | Violet, lighter than near RHS N87D, and fading darker, near RHS N87C. | Violet, near RHS 86C. |
| Venation color; upper petal surface, when fully open. | Purple-violet, near RHS N82C and N82D, and blotched violet, near RHS 86B and N87A. | Violet, in between near RHS 86A and N88A; slightly closer to N88A. |
| Venation color; lower petal surface, when fully open. | Violet, near RHS N88B. | Violet, near RHS 86A. |
| Labellum apex. | Central lobe is emarginate, and lateral lobes are obtuse. | Central lobe is strongly emarginate, and lateral lobes are emarginate. |
| Central lobe of labellum; color of the upper surface when fully open. | Violet, near RHS 86A, and fading to violet-blue at the apex, RHS N89B. | Violet-blue, in between near RHS N92A and N92C; base slightly lighter, near RHS 86A. |
| Central lobe of labellum; color of the lower surface when fully open. | Violet-blue, near RHS N92B, and fading lighter towards the base, near RHS 91C. | Violet, near RHS 86A, and fading lighter towards the base, near RHS 86D. |
| Dorsal sepal dimensions. | 4.9 cm long and 4.7 cm wide. | 4.6 cm long and 4.0 cm wide. |
| Lateral sepal dimensions. | 5.0 cm long and 5.6 cm wide. | 4.9 cm long and 4.6 cm wide. |
| Sepal color; upper surface, when opening. | Dorsal sepal is white, near RHS NN155D, and blotched violet, near RHS N87C and N87D; moderately to heavily dotted violet to violet-blue, in between RHS 83A and N92A. Lateral sepals are white, near RHS NN155D, and blotched violet, near RHS 86C and 86D; moderately to heavily dotted violet to violet-blue, in between RHS 83A and N92A. | Lateral sepals and dorsal sepal are violet, near N88C, and veined darker, RHS 86B to 86C. |
| Sepal color; lower surface, when opening. | Dorsal sepal is violet, near RHS 85C to 85D, and fading darker towards the apex, near RHS 86B to 86C. Lateral sepals are violet, near RHS 85C to 85D, and fading darker towards the apex, near RHS 86B to 86C. | Lateral sepals and dorsal sepal are violet, near N88C, and veined darker, RHS 86B to 86C. |
| Sepal color; upper surface, when fully open. | Dorsal sepal is white, near RHS NN155A, and blotched violet, RHS N88B; heavily dotted and marbled darker, near RHS 86A. Lateral sepals are white, near RHS NN155A, and blotched violet, RHS N88B; heavily dotted and marbled darker, near RHS 86A. | Dorsal sepal is violet, near RHS N87C. Lateral sepals are violet, in between near RHS N87C to N87D. |
| Sepal color; lower surface, when fully open. | Dorsal sepal is violet, near 85C and 85D, and fading darker towards the apex, near RHS N88C. Lateral sepals are violet, near 85C and 85D, and fading darker towards the apex, near RHS | Dorsal sepal is violet, in between near RHS N87B and N87C. Lateral sepals are violet, near RHS N87C. N88C. |
| Venation color; upper sepal surface, when fully open. | Dorsal sepal is white, near RHS NN155A, and blotched violet, RHS N88B; heavily dotted and marbled darker, near RHS 86A. Lateral sepals are white, near RHS NN155A, and blotched violet, RHS N88B; heavily dotted and marbled darker, near RHS 86A. | Dorsal sepal is violet, in between near RHS 86A and N87A. Lateral sepals are violet, near RHS 86A. |
| Venation color; lower sepal surface, when fully open. | Dorsal sepal is violet-blue, near RHS 90D, and fading violet towards the apex, in between near N88B and N88C. Lateral sepals are violet-blue, near RHS 90D, and fading violet towards the apex, in between near N88B and N88C. | Dorsal sepal is violet, in between near RHS 86A and 86B. Lateral sepals are violet, in between near RHS 86A and N88A. |
| Spur dimensions. | 0.6 cm long, 0.4 cm in diameter, and 0.5 cm in vertical height. | 0.8 cm long, 0.25 cm in diameter, and 0.5 cm in vertical height. |
| Spur shape. | Short triangular. | Flattened narrow triangular. |
| Spur color. | Violet, near RHS 85D, and very slightly striped darker, near RHS 85B to 85C. | Violet, near RHS 85B to 85C, and striped darker, near RHS N87C to N87D; apex is darker, near RHS 86B to 86C. |

That which is claimed is:

1. A new and distinct variety of *Vanda* plant named 'SPCDW1515', substantially as described and illustrated herein.

* * * * *